US005773007A

United States Patent [19]

Penney et al.

[11] Patent Number: 5,773,007
[45] Date of Patent: Jun. 30, 1998

[54] VACCINE COMPOSITIONS

[75] Inventors: Christopher L. Penney, Quebec; Francis Michon, Ottawa; Harold J. Jennings, Gloucester, all of Canada

[73] Assignee: National Research Council of Canada, Ottawa, Canada

[21] Appl. No.: 297,359

[22] Filed: Aug. 26, 1994

Related U.S. Application Data

[63] Continuation of Ser. No. 101,339, Aug. 2, 1993, abandoned, which is a continuation of Ser. No. 583,372, Sep. 17, 1990, abandoned.

[51] Int. Cl.[6] .................. A61K 39/09; A61K 39/085; A61K 39/108; A61K 47/42
[52] U.S. Cl. .................. 424/197.11; 424/278.1; 514/18; 514/19
[58] Field of Search .................. 530/328–331; 260/998.2; 514/18, 19; 560/38–40; 424/193.1, 194.1, 197.11, 278.1

[56] References Cited

U.S. PATENT DOCUMENTS

| | | | |
|---|---|---|---|
| 4,258,029 | 3/1981 | Moloney et al. | 424/88 |
| 4,428,932 | 1/1984 | Overell | 424/91 |
| 4,663,160 | 5/1987 | Tsay et al. | 424/87 |
| 4,695,624 | 9/1987 | Marburg et al. | 530/395 |
| 4,727,136 | 2/1988 | Jennings et al. | 530/395 |
| 4,761,283 | 8/1988 | Anderson et al. | 424/92 |
| 4,771,127 | 9/1988 | Cryz et al. | 530/395 |
| 4,789,735 | 12/1988 | Frank et al. | 530/395 |
| 5,019,383 | 5/1991 | Hopp | 424/88 |
| 5,026,546 | 6/1991 | Hilgers et al. | 424/88 |
| 5,034,519 | 7/1991 | Beuvery et al. | 536/117 |

FOREIGN PATENT DOCUMENTS

| | | |
|---|---|---|
| 0018189 | 10/1980 | European Pat. Off. . |
| 0177015 | 4/1986 | European Pat. Off. . |
| 0191536 | 8/1986 | European Pat. Off. ..... A61K 39/385 |
| 0273512 | 7/1988 | European Pat. Off. . |
| 0289110 | 11/1988 | European Pat. Off. . |
| 0336736 | 10/1989 | European Pat. Off. . |
| 0356340 | 2/1990 | European Pat. Off. . |
| WO 8802262 | 4/1988 | WIPO . |
| WO 9006696 | 6/1990 | WIPO . |

OTHER PUBLICATIONS

Geerligs et al., Journal of Immunological Methods 124: 95–102 (1989) "The Influence of Different Adjuvants on the Immune Response to a Synthetic Peptide Comprising Amino Acid Residues 9–21 of Herpes Simplex Virus Type 1 Glycoprotein D".

Hoffmann et al., Science 237: 639–642 (1987) "Naturally Acquired Antibodies to Sporozoites Do Not Prevent Malaria: Vaccine Development Implications".

Hokama, Y., and Nakamura, R., Immunology and Immunopathology: Basic Concepts, Little, Brown and Company, Boston, 1982, p. 73.

Kenney et al., Journal of Immunological Methods 121: 157–166 (1989) "Influence of Adjuvants on the Quantity, Affinity, Isotype and Epitope Specificity of Murine Antibodies".

Chemical Abstracts, vol. 105, No. 5, Aug. 4, 1986 (Columbus, Ohio, US) for Landi Article from Vaccine 4: 99–104, Abstr. #40693w.

Lehn et al., The Journal of Immunology 143: 3020–3024 (1989) "IL–4 Inhibits $H_2O_2$ Production and Antileishmanial Capacity of Human Cultured Monocytes Mediated by IFN–$\gamma^1$".

Matuhasi et al., J. Infectious Diseases 146, 290 (1982) "Evaluation of Levels of IgE Antibody to Tetanus Toxin in Individuals Vaccinated With Diphtheria–Pertussis–Tetanus Vaccine".

McConnell, The Immune System, A Course on the Molecular and Cellular Basis of Immunity, Blackwell Scientific Publications, Oxford, 1981, p. 9, Table I.3 "IgE subclasses in man and animals".

Mueller et al., The Journal of Immunology 40: 21–32 (1941) "Production of Diphtheric Toxin of High Potency (100 Lf) on a Reproducible Medium".

Murphy, S.G., Journal of Bacteriology 94: 586–589 (1967) "Tetanus Toxin and Antigenic Derivatives".

Norley et al., Immunobiol. 184: 193–207 (1992) "Vaccination Against HIV".

Odean et al., Infection and Immunity 58: 427–432 (1990) "Involvement of Gamma Interferon in Antibody Enhancement by Adjuvants".

Penney et al., Journal of Biol. Stand. 14: 345–349 (1986) "Analysis of the Immunoadjuvant Octadecyl Tyrosine Hydrochloride".

Chemical Abstracts, vol. 107, No. 20, Nov. 16, 1987 (Columbus, Ohio, US), for Penney article from J. Biol. Stand. 14: 345–9, #183681t.

Penney et al., Journal of Biol. Stand. 13: 43–52 (1985) "The Interaction of Slow–Release Immunoadjuvants With Selected Antigens Measured In Vitro".

Chemical Abstracts, vol. 103, No. 2, Jul. 15, 1985 (Columbus, Ohio, US) for Penney Aricle from J. Biol. Std. vol. 13: 43–52, #128859z.

1990 Physicians' Desk Reference, pp. 1182–1183.

Pillemer et al., The Journal of Immunology 54: 213–224 (1946) "The Immunochemistry of Toxins and Toxoids".

Roitt, Immunology, Gower Medical Publishing Ltd., 1985, Chapter 19, pp. 19.16—19.17.

Szu et al., J. Experimental Medicine 166: 1510–1524 (1987) "Capsular Polysaccharide–Protein Conjugates for Prevention of Typhoid Fever".

(List continued on next page.)

*Primary Examiner*—Mary E. Ceperley
*Attorney, Agent, or Firm*—Morgan & Finnegan, L.L.P.

[57] ABSTRACT

Improved vaccine compositions comprising a long chain alkyl compound as an immunoadjuvant in combination with a bacterial polysaccharide protein conjugate. The compositions of the invention are useful in activating the immune system to confer immunity to a host against the immunogen in a prophylactic manner.

23 Claims, No Drawings

OTHER PUBLICATIONS

Nixon–George et al (Jun. 1990) J. Immunol. 144:4798–4802.
Landi et al (1986) Vaccine 4:99–104.
Fattom et al (1988) Infect. Immunity 56(9):2292–2298.
Schneerson et al (1980) J. Expt. Med. 152: 361–376.
Penney et al (1985) J. Org. Chem. 50(9):1457–1459.
Wheeler et al (1984) Int. Arch. Allergy Appl. Immun. 75:294–299.

*Microbiology* Third Ed. B.D. Davis et al Harper & Row Pub. NY 1980 p. 436.

Liang et al. (1985) J. Immunol. 141:1495–1501.

*Dictionary of Immunology* Third Ed. Eds W.J. Herbert et al Blackwell Sci. Pub. Oxford 1985 pp. 4, 15, 16.

Arora et al (1988) Nat. Immun. Cell Growth Regul. 1: 287–296.

VACCINE COMPOSITIONS this application is a continuation of application Ser. No. 08/101,339, filed on Aug. 2, 1993, abandoned, which is a continuation of application Ser. No. 07/583,372, filed on Sep. 17, 1990, abandoned.

The present invention relates to vaccine compositions having improved immunogenicity. More particularly, the compositions of the invention comprise a bacterial polysaccharide covalently linked to a protein carrier in combination with a long chain alkyl compound. Both the carrier and the alkyl compound function as an adjuvant.

BACKGROUND OF THE INVENTION

It is well known that vaccines are important in the prophylaxis of disease. Vaccines operate by exposing a host animal to foreign material designed to activate the immune system to confer upon the host immunity against the material without exposing the host to the risk of disease. At the present time, about 20 vaccines have been developed for commercial use. Most of these vaccines are made by detoxification of the disease—causing organism, or a portion of that organism, or by isolation of a specific non-toxic portion of the organism. A well known example of the latter is the isolation of capsular polysaccharides from meningococcal and pneumococcal bacteria as the basis for a vaccine for bacterial meningitis and pneumonia. However, polysaccharide vaccines are poor immunogens which do not give rise to adequate amounts of protective antibodies in individuals with poorly developed or impaired immune systems. The latter includes young children, the elderly, or those with autoimmune diseases. Furthermore, the immune response which does occur is T-independent or non-memory which means the individual will not display an increased antibody response, with seroconversion, upon being given a booster injection. T-cell dependence is necessary for the induction of IgG antibodies and memory cells. Thus, upon seroconversion, both IgM and IgG antibodies are formed upon repeated injections of a vaccine. Furthermore, the magnitude of the antibody response increases with each injection of vaccine, when the response is T-dependent. The immunology of polysaccharide vaccines has been reviewed by Jennings et al, "The Polysaccharides" (Editor; G. O. Aspinall), Volume 1, 291–329 (1982).

Conjugation, or covalent bonding, of the polysaccharide to an appropriate protein carrier improves the immune function in that a T-dependent or memory response will occur. In December 1987, the first conjugate vaccine was approved for human use in the United States. This consisted of the H. influenzae b capsular polysaccharide covalently conjugated to a diphtheria toxoid carrier protein. The approval was for children 18 months of age, as the commercial polysaccharide vaccine was of limited efficacy at that age. Another H. influenzae b conjugate vaccine, prepared by means of a different conjugation chemistry, was recently approved in the U.S.

The polysaccharide and polysaccharide-protein conjugates are purer and hence safer vaccines than the classical whole bacterial or viral vaccines. That is, the latter are often contaminated with toxic by-products, even though the entire bacterium or virus has been biochemically detoxified by treatment with chemicals, heat or genetic attenuation. However, because of the improved purity of polysaccharide and polysaccharide-protein conjugates, which frequently means that natural immunostimulants have been removed, these new vaccines are often not optimally immunogenic. Natural immunostimulants include bacterial components such as lipopolysaccharide, lipoprotein and muramyl dipeptide; all of which are toxic. Further, the protein carrier can also have some degree of toxicity, thereby making it desirable to use as small an amount as possible. For example, diphtheria toxoid, and the related molecule CRM 197, are commonly employed carrier molecules for conjugate vaccines for human use. However, adults can display local or general hypersensitivity reactions to these carrier molecules. In order to offset these effects, adjuvants are employed in association with the vaccines to elicit enhanced antibody formation. Adjuvants also offer the possibility of influencing the type of antibody produced in response to the vaccine. For example, although seroconversion and subsequent production of IgG antibody will occur upon immunization with a polysaccharide-protein conjugate vaccine, the response will be primarily IgG1 in the mouse. An increase in the production of IgG2a antibody would be beneficial as the latter is the most effective murine antibody with regard to activation of complement. The complement pathway provides an important defense mechanism against many bacterial infections.

As regards adjuvants for commercial use, only aluminum and calcium salts are presently employed as adjuvants. However, aluminum and calcium salts are not potent adjuvants. Calcium salts have found only limited use. While aluminum salts have found more widespread use with other vaccines, little success has been reported with polysaccharide-protein conjugate vaccines. In fact, it has been reported that aluminum hydroxide inhibits the antibody response to an H. influenzae b polysaccharide-tetanus toxoid conjugate vaccine; Clauesson, et al, J. Pediatrics, 112, 695–702 (1988). J. B. Robbins, et al also observe the same suppression of the antibody response with aluminum hydroxide and a S. Typhi polysaccharide—cholera toxin conjugate vaccine; J. Experimental Medicine, 166, 1510–1524 (1987). Furthermore, aluminum salts may provoke transient or chronic local granulomas at the site of injection; L. H. Collier in Lancet, 1354–1367 (1987) states that the incidence and severity of reactions to tetanus toxoid vaccine depends upon the presence of aluminum adjuvant. The preparation of aluminum adjuvants is not always reproducible. Moreover, aluminum can alone stimulate the production of IgE antibodies which are responsible for mediating immediate hypersensitive reactions. This has been described by T. Matuhasi et al, J. Infectious Disease, 146, 192 (1982).

Attention has focused in recent years on the use of organic compounds as adjuvants. Only a few organic compounds function in a manner similar to commercially acceptable aluminum salts; i.e. as a slow release vehicle or antigen (vaccine) depot whereby antigen is released over a relatively long period of time at the site of injection.

Examples of such organic compounds are organic surfactants and emulsifiers, such as Pluronics and Tetronics which are non-ionic block copolymers of polyoxyethylene and polyoxypropylene produced by BASF Corporation. Such a slow-release mechanism of adjuvanticity has long been accepted for human use since it reduces the possibility of overstimulating the immune system. Overstimulation of the immune system can lead to an autoimmune response such as would occur with the use of a potent immunostimulant, for example Freund's adjuvant. Thus, the slow release mechanism is the preferred mechanism.

While the majority of organic adjuvants have been shown to be potent immunostimulants, such highly active adjuvants tend to be toxic and therefore unacceptable for human use. Examples of known organic adjuvants which are potent immunostimulants are Freund's complete adjuvant and muramyl dipeptide. Both of these compounds are restricted to use in animal research because of toxicity considerations. Many of the organic adjuvants which mimic aluminum salts are more toxic than aluminum salts. For example, long chain alkyl amines described by D. Gall in Immunology, 11, 369–386 (1966) are reported to be toxic compounds which are generally disruptive to cell membrane structure.

It is known that the octadecyl ester of the amino acid tyrosine is an adjuvant. It has minimal immunostimulatory properties, but instead functions as an organic equivalent to aluminum adjuvants—a slow release vehicle. That is, antigens will complex with octadecyl tyrosine, to be slowly released or desorbed from the insoluble adjuvant with time. The complexation between the antigen and adjuvant occurs through a variety of weak, non-covalent forces, such as hydrophobic interactions and hydrogen bonding.

This phenomenon is seen in U.S. Pat. No. 4,428,932 to Overell and U.S. Pat. No. 4,258,029 to Moloney et al. Overell discloses that octadecyl tyrosine functions as an adjuvant for allergy desensitization therapy when complexed with allergens such as rye, grass and pollen extract. Moloney et al teach that octadecyl tyrosine functions as an adjuvant for vaccines when complexed with tetanus toxoid and formalin inactivated type I, II and III poliomyelitis virus. The phenomenon is further described by A. Nixon-George et al, J. Immunology, 144, 4798–4802 (1990), who disclose that octadecyl tyrosine, and other octadecyl esters of aromatic amino acids, function as an adjuvant for a candidate vaccine for heptitis B upon complexation with a recombinant hepatitis B surface antigen.

A need exists therefore to develop non-toxic bacterial polysaccharide protein conjugate vaccine—adjuvant compositions having improved immunogenicity.

SUMMARY OF THE INVENTION

The present invention centers on improved vaccine compositions comprising a non-toxic bacterial polysaccharide-protein conjugate vaccine and a non-toxic long chain alkyl adjuvant. Thus, according to one aspect of the present invention, there is provided a vaccine composition comprising a non-toxic bacterial polysaccharide protein conjugate and an adjuvant which is a non-toxic long chain alkyl compound present in an amount effective to amplify the immunogenicity of the polysaccharide-protein conjugate.

According to another aspect of the invention, there is provided a method of eliciting an immune response in a warm blooded animal, including humans, comprising administering to the host animal an effective amount of a vaccine composition of the invention.

It has surprisingly been found, according to the present invention, that non-toxic long chain alkyl compounds, in particular esters of amino acids or peptides, can complex with polysaccharide-protein conjugate vaccines. As a consequence of this complexation, the long chain alkyl compounds function as a slow release vehicle. That is, the long chain alkyl compounds release the conjugate vaccine over an extended period of time into the host animal. This results in an increased antibody response, relative to that produced by the conjugate vaccine alone. As noted above, this mechanism of adjuvanticity is the same as that which is observed with aluminum salts and non-conjugated vaccines. However, as also noted above, aluminum salts are, for the most part, ineffective adjuvants for bacterial polysaccharide-protein conjugate vaccines. It would therefore not have been expected that the long chain alkyl compounds of this invention, by virtue of the same mechanism of adjuvanticity, would function as adjuvants for conjugate vaccines. It is therefore even more surprising that the non-toxic long chain alkyl compounds function to improve the immunogenicity of the conjugate vaccines.

It has also been found according to the present invention that the presence of a non-toxic long chain alkyl compound as adjuvant, typically a long chain alkyl amino acid or peptide ester, influences the isotype of antibody produced in response to the conjugate vaccine. Specifically, the ratio of IgG2a antibody to IgG1 antibody is higher in that both antibody isotype levels are increased when long chain alkyl adjuvants are used with the conjugate vaccines in accordance with the invention as opposed to the ratio observed when no adjuvant is present. This ratio increase is of beneficial effect since IgG2a antibody is important as being the most effective murine antibody in regard to activation of complement and antibody-dependent cellular cytotoxicity mechanisms and protection against tumors and parasites.

The adjuvant effect of the long chain alkyl compound, in terms of the increase and modulation (i.e. isotype change) of the antibody response, is also surprising in terms of the role of the carrier protein. That is, it is the function of the carrier within the conjugate vaccine to increase and modulate the antibody response.

Therefore, unlike aluminum adjuvants, the long chain alkyl compound is enhancing the carrier function.

The non-toxic long chain alkyl compound is preferably a positively charged ester of an amino acid or peptide, in particular an ester of an alkyl alcohol containing 14 to 20 carbon atoms and an amino acid, dipeptide or tripeptide.

DETAILED DESCRIPTION OF THE INVENTION

The bacterial polysaccharide protein conjugate employed in the compositions of the invention is capable of eliciting an immune response in the host. As used herein, the term "bacterial" includes capsular polysaccharides, lipopolysaccharides and other subcapsular (surface) polysaccharides. In particular, capsular polysaccharides from pathogenic bacteria are presently the most useful for the manufacture of effective conjugate vaccines. Examples of such capsular polysaccharides include those isolated from *Haemophilus influenzae, Neisseria meningitidis, Streptococcus pneumoniae, Streptococcus agalactiae, Salmonella typhi, Escherichia coli*, and *Staphylococcus aureus*. Examples of lipopolysaccharides are those isolated from *Neisseria meningitidis, Escherichia coli, Salmonella typhi*, and *Pseudomonas aeruginosa*. Examples of other subcapsular polysaccharides are the common polysaccharide antigen (c-substance) of Group A, B and C Streptococci and the common polysaccharide antigen (c-substance) of *Streptococcus pneumoniae*.

The examples which follow describe experiments with conjugates comprising polysaccharides of significantly different chemical structure, namely Meningococcal group A polysaccharide (a homopolymer of N-acetyl mannosamine 6-phosphate), Meningococcal group B (a homopolymer of (2→8) linked N-butanoyl neuraminic acid) and Meningococcal group C (a homopolymer of (2→9) linked N-acetyl neuraminic acid). It is to be understood that the present invention is not limited to the exemplified Meningococcal conjugates and also applies to conjugates comprising other bacterial polysaccharides as defined and exemplified above.

The bacterial polysaccharides employed in the conjugates in this invention are readily prepared using conventional isolation techniques.

The carrier molecules to which the bacterial polysaccharides are conjugated or covalently linked are proteins. Preferred carriers for animal use are bovine serum albumin and Keyhole Limpet Hemocyanin. Protein carriers suitable for human use include tetanus toxoid, diphtheria toxoid, acellular pertussis vaccine (LPF toxoid), cross-reacting materials (CRM's) which are antigenically similar to bacterial toxins but are non-toxic by means of mutation, preferably CRM 197 obtained according to Pappenheimer, et al, Immunochemistry, 9, 891–906 (1972), and other bacterial protein carriers, for example meningococcal outer membrane protein. Preferably, the carrier protein itself is an immunogen.

The polysaccharide may be covalently coupled to the carrier by any convenient method known to the art. While use of a symmetric linker such as adipic acid dihydrazide, as described by Schneerson et al, J. Experimental Medicine, 152, 361–376 (1980), or a heterobifunctional linker such as N-succinimidyl 3-(2-pyridyldithio) propionate as described by Fattom et al, Infection and Immunity, 56, 2292–2298 (1988) are within the scope of the invention, it is preferred to avoid the use of any linker but instead couple the polysaccharide directly to the protein carrier by means of reductive amination as described by Landi et al J. Immunology, 127, 1011–1019 (1981).

The size of the bacterial polysaccharide, as defined by average molecular weight, is variable and dependent upon the bacteria from which it is derived and the method of coupling of the polysaccharide to the carrier. Therefore, it can be as small as 1,000 daltons ($10^3$) or greater than $10^6$. With the reductive amination coupling method, the polysaccharide molecular weight is usually within the range of 5,000 to 500,000, for example 300,000 to 500,000, or for example 5,000 to 50,000 daltons.

The long chain alkyl adjuvant, as well as any compounds which arise from its metabolism in the host, should be non-toxic. It is well known that long chain fatty alcohols are naturally occurring non-toxic substances. As an example, octadecanol is found to be totally non-toxic in humans, as is indicated by an oral LD50 which is greater than 15 g/kg as found in Gosselin's "Clinical Toxicology of Commercial Products", Fourth Edition 1976. Octadecyl tryrosine has been found to be non-toxic in animals and the majority of naturally occurring amino acids are non-toxic; C. L. Penney et al, Vaccine, 4, 99–104 (1986). It would therefore be expected that octadecyl tyrosine and esters of other alcohols and amino acids would not exhibit any toxicity in humans.

The adjuvant should be capable of forming microparticles having a size of between about 150 $\mu$m–1 mM (mesh 18-mesh 100, preferably about 250 $\mu$M, or mesh 60) in an aqueous medium, thereby giving rise to a suspension of uniform consistency. Moreover, the adjuvant microparticles should permit absorption of the conjugate vaccine, thereby allowing the slow release of conjugate into the host.

In a preferred embodiment of the present invention, the adjuvant is a compound of formula:

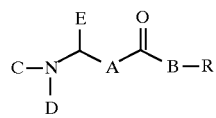

where C is a hydrogen atom, an amino acid residue, or peptide residue including up to ten amino acid residues (i.e. up to a decapeptide); D is a hydrogen atom, or a pharmaceutically acceptable acid such as hydrochloric, hydrobromic, phosphoric, sulphuric, tartaric, lactic or acetic acid. E is 4-hydroxybenzyl, benzyl, 4-hydroxyphenyl, phenyl, 4-aminobutyl, isopropyl, methyl, hydrogen or other residue of a naturally occurring amino acid; A is $(CH_2)_n$, oxygen or $CH_2O$ and B is $(CH_2)_n$ or oxygen, where n is 0 to 4, but A≠B for $(CH_2)_n$ or oxygen; and R is an alkyl group containing 12 to 20 carbon atoms.

Preferably, C may be either hydrogen, an amino acid, a dipeptide or a tripeptide. If C is an amino acid, the amino acid sequence of the adjuvant may be selected from for example tyrosyl glycine, glycyl glycine, glycyl tyrosine, and phenylalanyl glycine.

If C is a dipeptide, the amino acid sequence of the adjuvant may be selected from for example tyrosyl glycyl glycine or tyrosyl alanyl glycine. If an amino acid residue is chiral, the D-enantiomer, the L-enantiomer, or mixtures thereof may be employed. It is particularly preferred for the adjuvant to comprise an alpha amino acid.

It is particularly preferred for E to be selected from 4-hydroxybenzyl, benzyl, 4-hydroxyphenyl, phenyl and hydrogen. E is most preferably 4-hydroxybenzyl.

When A is $CH_2O$ and B is $(CH_2)_n$, the compounds are N-aminoacylethanolamine-O-stearates. When A is $CH_2O$ and B is oxygen, the compounds are carbonates.

More preferably, the adjuvant is an amino acid ester hydrochloride where C is hydrogen, D is hydrochloric acid, A is $(CH_2)_n$, where n is 0–4, and B is oxygen.

Most preferably, the adjuvant is octadecyl tyrosine hydrochloride where C is hydrogen, D is hydrochloric acid, E is 4-hydroxybenzyl, and R is octadecyl, A is $(CH_2)_n$ where n is zero and B is oxygen.

Generally, when C is not hydrogen, the backbone of the adjuvant comprises substantially peptide bonds, i.e., the carboxylate of one amino acid residue is linked directly to the amino of the adjacent residue, in a head-to-tail manner. Alternatively, the peptide bond may be a thioamide.

The adjuvant may be prepared by any convenient method. For example, the amino ester portion of the adjuvant may be synthesized by any one of a number of established methods, as has been described by M. Bodansky et al "Peptide Synthesis" Second Edition, Wiley, New York 1976 and R. W. Roeske, Peptides (N.Y.) 3, 102 (1981). A particularly preferred method is the methanesulfonic acid catalyzed esterification procedure described by C. Penney et al, J. Organic Chemistry 50, 1457–1459 (1985).

When the adjuvant is a di- or tripeptide, the peptide bonds may be formed by any of the procedures described in "Peptides Synthesis" mentioned above. Additionally, the peptide bonds may be formed following either solid or solution phase protocols. Many protocols and reagents exist which are useful in forming amide, thioamide, or thioester bonds.

During the preparation of the adjuvant, it may be desirable to temporarily protect reactive functional groups. For example, amines may be protected by urethane-type groups, alcohols by t-butyl or benzyl groups, and acids by ester groups. Suitable protection-deprotection conditions and protocols are described in "Peptide Synthesis" mentioned above.

The adjuvant may be purified by any of the techniques described previously. The preferred purification technique is silica gel chromatography, in particular the "flash" (rapid) chromatographic technique, as described by W. Clark Still et al, J. Organic Chemistry, 43, 2923–2925 (1978). However, other chromatographic methods, including HPLC, may be used for purification of the adjuvant. Crystallization may also be used to purify the adjuvant. In some cases, no purification is required as a product of analytical purity is obtained directly from the synthesis.

The vaccine compositions of the invention are prepared by physically mixing the adjuvant with the polysaccharide-carrier protein conjugate under appropriate sterile conditions in accordance with known techniques to produce the adjuvanted composition. Complexation of the polysaccharide-carrier protein conjugate and the adjuvant is facilitated by the existence of a net negative charge on the conjugate which is electrostatically attracted to the positive charge present on the long chain alkyl compound adjuvant.

The amounts of the adjuvant and polysaccharide-carrier protein conjugate needed to elicit an immune response in humans are interrelated, but are within the ranges generally employed in conventional vaccines. For example, the use of increasing amounts of adjuvant may suggest that decreasing amounts of conjugate can be used, and vice versa. The preferred amount of adjuvant is 0.01 to 5 mg/ml of the composition, for example 0.05 mg/ml to 3 mg/ml, preferably 0.5 to 1.0 mg/ml. The preferred amount of conjugate is between about 1 to 100 micrograms/ml, preferably about 5 to 40 micrograms/ml. The dosage will depend upon the host receiving the vaccine as well as factors such as the size, weight, and age of the host.

The vaccine compositions of this invention may be formulated using techniques similar to those used for other pharmaceutical polypeptide compositions. Thus, the adjuvant and conjugate may be stored in lyophilized form and reconstituted in a physiologically acceptable vehicle to form a suspension prior to administration. Alternatively, the adjuvant and conjugate may be stored in the vehicle. Preferred vehicles are sterile solutions, in particular, sterile buffer solutions, such as phosphate buffered saline. Any method of combining the adjuvant and the conjugate in the vehicle such that immproved immunological effectiveness of the composition relative to the individual components is appropriate.

The vehicle may contain preservatives or other known additives which are used to improve the shelf stability or the efficacy of the mixture. Suitable preservatives include, for example, thimerosal.

The volume of a single dose of the vaccine of this invention may vary but will be generally within the ranges commonly employed in conventional vaccines. The volume of a single dose is preferably between about 0.1 ml and about 1.5 ml, more preferably between about 0.2 ml and about 0.5 ml at the concentrations of conjugate and adjuvant noted above.

The vaccine compositions of the invention may be administered by any convenient means. Preferred methods of administration include subcutaneous, intramuscular, intradermal, or by way of nasal delivery. Alternatively, the mixture may be released from a biodiffusible implant. A single administration may be used. Alternatively, a series of administrations may be made over the course of several days or weeks.

EXAMPLES

The following non-limiting examples illustrate the invention.

EXAMPLE 1

The following describes the isolation, preparation and conjugation of the Meningococcal group A and C polysaccharides.

The polysaccharides are obtained from the culture extracts of *N. meningitidis* strain 604 A for group A, and 2241C for group C. These strains were obtained from the culture collection of the Laboratory Center for Disease Control, Ottawa, Ontario, and were grown in a chemically defined medium as described in Kenny et al, Bull. W.H.O. 37:569 (1957). After fermenter growth (15 h) the bacteria were killed by the addition of formalin to a final concentration at 0.75%. The bacteria were removed by continuous centrifugation and the polysaccharides were isolated from the supernatant and purified essentially as described in Bundle et al, J. Biol. Chem. 249:4797–4801 (1974) except that the protein was extracted by stirring a solution of the crude polysaccharide with cold (4° C.) 90% phenol instead of hot (50°–60° C.) phenol. This modification ensures that a high molecular weight form of the polysaccharides is produced and isolated.

Depolymerization of the group A polysaccharide

Native meningococcal group A polysaccharide (average M.W. 30,000; 150 mg) was dissolved in 20 ml of sodium acetate buffer (100 mM; pH 5.0) and heated at 70° C. The depolymerization was monitored by FPLC (Pharmacia) on a SUPEROSE 12 cross-liked agarose based media having a bead size of approximately 10 microns and a pressure tolerance of 30 bars, gel exclusion column until the desired molecular weight (M.W. 12,000) was obtained. The material was dialyzed against distilled water at 4° C. and lyophilized to give 13.5 mg of an amorphous solid.

Reduction of the depolymerized group A polysaccharide

Depolymerized group A polysaccharide (100 mg) was dissolved in 3 ml tris (HCl) buffer (200 mM; pH 7.2) and cooled to 0° C. 5×2.5 mg aliquots of sodium borohydride were added to the stirred solution over 3 hours. The pH of the solution was maintained between 7.5–7.8 with the addition of 100 mM acetic acid. Then the pH of the solution was lowered to 5.5 with 1M acetic acid to destroy any residual borohydride and then raised to 7.5 with 100 mM sodium hydroxide. The solution was desalted on a BIO-GEL P6DG polysaccharide gel having a standard mesh when hydrated of 80 to 170 and a diameter of hydrated beads of 92 to 180 microns and a fractionation range of 1,000 to 6,000 daltons (Bio-Rad) column (1.6×100 cm) and eluted with water. The void volume peak was collected and lyophilized and to give 11.7 mg of reduced product.

Activation and Sizing of GAMP

Depolymerized and reduced group A polysaccharide (110 mg) was dissolved in 50 mM sodium periodate solution (2 ml) and kept in the dark for 1 hr at ambient temperature. Ethylene glycol (50 $\mu$l) was then added and the solution was allowed to sit at ambient temperature for 1 hour. The solution was desalted using a column of BIO-GEL P6DG (1.6×100 cm) Bio-Rad in water. The void volume peak was collected and lyophilized to afford 108 mg at oxidized product. The material was sized on a column of BIO-GEL A 0.5 (1.6×100 cm; 200–400 mesh $\leq$10,000–500,000 fractionation range, in PBS Bio-Rad). Fractions eluting from the column at $K_D$ 0.5 to $K_D$ 0.6 (average M.W. 10,000–15,000) as measured by FPLC (Pharmacia) on a column of SUPEROSE 12 (HR 10/30; Pharmacia), were collected, dialyzed and lyophilized.

Oxidation, depolymerization of the group C polysaccharide

Native meningococcal group C polysaccharide (200 mg) was dissolved in 20 ml water to which 2 ml of 100 mM sodium periodate solution (200 $\mu$M) was added. The depolymerization reaction was monitored by FPLC analysis as described for the group A polysaccharide. When the desired range of average molecular weight was obtained, the reaction was stopped with ethylene glycol (100 $\mu$l) and the solution was left at ambient temperature for 1 hour then dialyzed and freeze dried.

Sizing of the oxidized fragments of the GCMP

The oxidized GCMP was sized by gel filtration using a BIO-GEL A 0.5 column (1.6×100cm; 200–400 mesh) (Bio-Rad) in PBS. Fractions eluting from the column at $K_D$ 0.5 to $K_D$ 0.6 (average M.W. 10,000–15,000) as measured by FPLC (as described above) were collected, dialyzed and lyophilized. The GCMP fragments thus collected contain aldehyde at both termini.

Polysaccharide conjugates

The oxidized fragments of either A or C polysaccharides (90 mg) were dissolved in 100 mM $NaHCO_3$ (pH 8.1) buffer (2 ml), and tetanus toxoid monomer (30 mg) was added to the solution. Following the addition of sodium cyanoborohydride (Aldrich, Milwaukee, Wis.; 60 mg), the solutions were incubated at 37° C. for 4 days. The reaction mixtures were then applied directly to BIO-GEL A (0.5) (200–400 ml; 1.6×100 cm) (Bio-Rad) columns in PBS. The elements containing the conjugates were dialyzed against distilled water and lyophilized. The conjugates had a molar ratio of polysaccharide to tetanus toxoid of 2–3:1 respectively.

EXAMPLE 2

The following describes the preparation of and conjugation of N-propionyl and N-butanoyl Group B Meningococcal polysaccharides.

Propionic and butanoic anhydrides together with colominic acid were obtained from Sigma Chemicals Co., St. Louis, Mo. Because colominic acid is structurally identical to the group B meningococcal polysaccharide (GBMP), it is referred to henceforth as GBMP. Tetanus toxoid was obtained from the Institut Armand-Frappier, Laval, Quebec, and its monomeric form, used in all the conjugations, was obtained by passage of the above preparation through a BIO-GEL (trademark) A 0.5 (200–400 mesh) column (1.6× 90 cm) (Bio-Rad, Richmond, Calif.), equilibrated and eluted with 0.01M phosphate buffered physiologic saline (PBS) (pH 7.4).

N-Deacetylation of the GBMP

The GBMP ($Na^+$ salt) (1.0 g) was dissolved in 5 ml of 2M NaOH and, following the addition of $NaBH_4$ (150 mg), the solution was heated at 110° C. for 6 hours in a screw cap TEFLON (trademark) container (60 ml). This procedure is essentially as described in J. Immunol., 134, 2651 (1985) and U.S. Pat. No. 4,727,136, both in the name of Harold J. Jennings et al. The cooled diluted solution was then exhaustively dialyzed against distilled water at 4° C., and lyophilized. The fact that N-deacetylated GBMP was obtained was determined by the absence of the methylacetamido signal (singlet at delta 2.07) in the $^1H$-nmr spectrum of the N-deacetylated GBMP.

N-Acylations of the GBMP

N-deacetylated GBMP (1.0 g) was dissolved in 50 ml of 5% aqueous $NaHCO_3$. To the two individual aliquots (10 ml of the above solution) were added either propionic or butanoic anhydrides. These reagents were added in 3×0.5 ml aliquots over a 3 hour period of time at room temperature while the solution was maintained at pH 8.0 with 0.5N NaOH. Methanol (0.5 ml) was added simultaneously with each addition of anhydride in order to increase their solubility. Finally the solutions were stirred for 16 hours at 4° C., exhaustively dialyzed against distilled water at 40° C., and lyophilized. The individual N-propionylated and N-butanoylated GBMP were obtained in yields in excess of 90%. In each case, essentially complete N-acylation was confirmed by the disappearance in the respective $^1H$-nmr spectrum of N-deacetylated GBMP.

Activation of N-Acylated GBMP

Terminal aldehyde groups were introduced into the N-acylated GBMP by periodate oxidation. The N-acylated GBMP's obtained as above were oxidized in 0.1M aqueous sodium metaperiodate (10 ml) for 2 hours at room temperature in the dark. Excess periodate was then destroyed by the addition of 1 ml of ethylene glycol and the solution was then exhaustively dialyzed at 4° C., and lyophilized. The use of sodium borohydride in the N-deacetylation procedure (except for the GBMP) results in the transformation of the terminal reducing sialic acid residues of each of the N-acylated GBMP, to open chain polyol residues. This type of residue is periodate sensitive (see J. Immunol., 127, 1011 (1981) and U.S. Pat. No. 4,356,170 to Harold J. Jennings et al), thereby resulting in the introduction of aldehyde groups into the N-acylated GBMP's at both termini.

Sizing of the different N-acylated GBMP

Gel filtration, using an ULTRAGEL (trademark) AcA 44 (bead diameter 60–140 μm) column (IBF Biotechnics, Savage, Md.) with PBS as eluant, was employed to obtain the desired average molecular weight oxidized N-acylated GBMP material. Fractions eluting from the column at $K_D$ 0.5 to $K_D$ 0.7 as measured by FLPC (see below) were collected, dialyzed, and lyophilized. This range of $K_D$ 0.2 to 0.4 corresponding to fragments having an average molecular weight in the range of 30,000 to 40,000 daltons have also been collected and conjugated. Thus, N-acylated material eluting in the $K_D$ range of 0.2 to 0.7 is of particular interest.

Polysaccharide Conjugates

The oxidized fragments (100 mg) were dissolved in 0.1M sodium bicarbonate (pH 8.1) buffer (2 ml) and tetanus toxoid (20 mg) was added to the solution. Finally, following the addition of sodium cyanoborohydride (40 mg), the solution was gently stirred at room temperature. The course of the conjugation was followed by FPLC using a gel filtration column containing SUPEROSE (trademark) 12 HR10/30 (Pharmacia), run isocratically at 1 ml/min in PBS buffer at pH 7.2, both the protein and N-acylated GBMP fragments being monitored at 214 nm. The fragments had $K_D$ 0.6, and tetanus toxoid had $K_D$ 0.39. In most cases, the conjugations were complete in 2 days but were left for a total reaction time of 4 days. The potential unreacted aldehyde groups were finally reduced with sodium borohydride (20 mg) prior to gel filtration.

The polysaccharide tetanus toxoid conjugates were separated from the polysaccharide fragments by gel filtration using a BIO-GEL A column with PBS as eluant. The eluant containing the conjugate was dialyzed against distilled water and lyophilized. The N-acylated GBMP tetanus toxoid conjugates contained from 12–30%, typically 12–20%, sialic acid as determined by the resorcinol method described by Svennerholm, L., Quantitative Estimation of Sialic Acids, II A Colorimetric Resorcinol-Hydrochloric Acid Method, Biochim, Biophys. Acta 24, 604 (1957). This indicates that the conjugates had a molar ratio of polysaccharide to tetanus toxoid of 2–3:1 respectively.

EXAMPLE 3

The following describes the general method for the complexation of a polysaccharide-protein carrier conjugate with a long chain alkyl amino acid or peptide ester adjuvant.

The long chain alkyl ester adjuvant was crushed and meshed, and an appropriate amount weighed into a vial such that the concentration of the suspension after addition of phosphate buffer saline (10 mM phosphate, pH=7.4) was 1–2 mg compound/ml. The suspension was thoroughly mixed, and then an equal volume of conjugate, in the same buffer, was added and the whole gently shaken for 16 hours at 4° C. At the end of the complexation, if it was desired to measure the amount of conjugate complexed to the adjuvant, the suspension was centrifuged and the concentration of conjugate (protein carrier) in the supernatant determined by the method of Lowry et al, J. Biological Chemistry, 193, 265–275 (1951) to give the amount of unbound conjugate. Generally, 30%–90% bound conjugate represents a good adjuvant-polysaccharide conjugate complex. Both the bound and unbound conjugate was used for the immunization experiments.

EXAMPLE 4

This example demonstrates the adjuvanticity of several long chain (18 carbon atoms) esters with meningococcal polysaccharide-tetanus toxoid conjugate vaccines.

Female white CF1 mice, 8 to 10 weeks old, were immunized via intraperitoneal injection with approximately 15 μg of conjugate per animal (approximately 3 μg of polysaccharide) on days 0, 14 and 28. The mice were bled on day 39 by heart puncture. The total volume per injection was always 0.2 ml, in either the presence or absence of adjuvant for the control mice.

The meningococcal polysaccharides were conjugated to the toxoid carrier by the reductive amination coupling method, as referred to above. The chemically modified meningococcal B polysaccharide was prepared as described above.

The antibody concentration in the sera was determined by enzyme immunoassay as follows; 96-well polystyrene plates (Corning) were coated with the appropriate capsular polysaccharide-bovine serum albumin conjugate in phosphate buffer saline (10 mM phosphate, pH=7,4), at a concentration of 1 μg/well, for an hour at 37° C. The plates were then blocked for one hour at 37° C. with 0.1% bovine serum albumin in phosphate buffer saline. After blocking, the plates were emptied and washed four times with phosphate buffer saline which contained 0.05% TWEEN 20 detergent (PBST). To the empty wells was added the sample(s) for analysis, and this was incubated for one hour at ambient temperature. After five washes with PBST, peroxidase labeled goat antimouse IgG (H+L) conjugate, 1/200 in PBST, was added to each well, and the plates incubated for one half an hour at ambient temperature. After another five washes with PBST, tetramethylbenzidine was added to each well, and the plates incubated for ten minutes at ambient temperature. The enzyme catalyzed reaction was stopped with 1M. phosphoric acid, after which the absorbance at 450 nm of each well was read with a plate reader (Biotek). Antibody titers are the reciprocal of the sample dilution which gave an absorbance of 1.0. The titers are expressed as a ratio relative to the control (no adjuvant). The results are presented in Table 1.

TABLE 1

Antibody response to meningococcal conjugate vaccines in the presence of long chain (C 18) esters. Titers are given as a ratio of the antibody response in the absence of adjuvant (control; conjugate vaccine in buffered saline).

| Adjuvant | Meningococcal Conjugate | | |
|---|---|---|---|
| | A. | B. (butanoyl) | C. |
| Control (PHS) | 1.0 | 1.0 | 1.0 |
| Octadecyl Tyrosine | | | |
| 0.5 mg/ml | 3.5 | 1.3 | 1.9 |
| 1.0 mg/ml | 3.7 | 1.9 | 3.2 |
| Octadecyl Tyrosyl Glycine | | | |
| 0.5 mg/ml | 3.0 | 1.8 | 1.9 |
| N. Glycylethanolamine O-Stearate | | | |
| 0.5 mg/ml | 1.0 | 1.5 | 1.0 |
| Octadecyl Lysine | | | |
| 1.0 mg/ml | N.D. | 1.3 | 1.8 |
| Octadecyl Forphenicine | | | |
| 1.0 mg/ml | N.D. | 1.9 | 1.8 |

N.D. = Not determined

The results in Table 1 show that long chain esters do display an adjuvant effect on bacterial polysaccharide-tetanus toxoid conjugates which is dependent upon the type of ester and type of bacterial polysaccharide present. This is a specific phenomenon. This can be seen by comparison of octadecyl tyrosine and N-glycylethanolamine O-stearate meningococcal A and C conjugates.

EXAMPLE 5

This example demonstrates the change in isotype which occurs in going from no adjuvant to an adjuvanated meningococcal polysaccharide-tetanus toxoid conjugate vaccine.

Immunizations of white CF1 mice were undertaken, and sera obtained as described in Example 4. 96-well polystyrene plates (Corning) were coated with the appropriate meningococcal polysaccharide-bovine serum albumin conjugate in phosphate buffer saline (10 mM phosphate, pH=7.4), as described in Example 4. The plates were blocked for one hour at 37° C., followed by one half hour at ambient temperature, with 2.5% skim milk in phosphate buffer saline.

After four washes with PBST, the sample(s) for analysis of isotype was added, and this was incubated for one hour at ambient temperature. After five washes with PBST, rabbit antimouse subclass specific probe (Bio-Rad Laboratories), Mouse Typer sub-isotyping panel was added to each well and the plates incubated for one hour at ambient temperature. After five more washes with PBST, peroxidase labeled goat antirabbit (IgG (H+L) conjugate, 1/3000 in PBST, was added, and the plates incubated for one half hour at ambient temperature. After another five washes with PBST, tetramethylbenzidine was added to the wells, the plates incubated for six minutes at ambient temperature, and the reaction stopped by the addition of 1M. phosphoric acid. The absorbance at 450 nm of each well was read with a plate reader (Biotek). Antibody titers are the reciprocal of the sample dilution multiplied by the absorbance. The titers are expressed as a ratio relative to the control (no adjuvant). The results are presented in Table 2.

TABLE 2

Isotype variation of the anti-meningococcal A and C conjugate response. Titers are given as a ratio of the antibody and in the absence of adjuvant (control; conjugate vaccine in buffered saline). Concentration of adjuvants is 0.5 mg/ml.

| Adjuvant | IgG1 | IgG2a | IgG2b | IgG3 | IgM |
|---|---|---|---|---|---|
| Immunoglobulin (Meningococcal A) | | | | | |
| Control (PBS) | 1.0 | 1.0 | 1.0 | 1.0 | 1.0 |
| Octadecyl Tyrosine | 2.6 | 5.7 | 4.3 | 4.4 | 3.4 |
| Octadecyl Tyrosyl Glycine | 1.6 | 3.9 | 3.6 | 2.6 | 1.6 |
| N-Glycylethanolamine O-Stearate | 1.0 | 1.0 | 1.0 | 1.0 | 1.0 |
| Immunoglobulin (Meningococcal C) | | | | | |
| Control (PBS) | 1.0 | 1.0 | 1.0 | 1.0 | 1.0 |
| Octadecyl Tyrosine | 2.1 | 5.2 | 2.3 | 4.3 | 1.7 |
| Octadecyl Tyrosyl Glycine | 2.1 | 2.9 | 1.9 | 2.9 | 1.7 |
| N-Glycylethanolamine O-Stearate | 1.0 | 1.0 | 1.0 | 1.0 | 1.0 |

The results in Table 2 show that long chain esters do influence the isotype distribution in a favorable manner. This can be seen by examination of the ratio of IgG2a/IgG1 (=2.2 for anti-meningogococcal A; =2.5 for anti-meningococcal C) in the presence of octadecyl tyrosine adjuvant.

EXAMPLE 6

This example demonstrates that the increased antibody response in the presence of a long chain ester adjuvant translates into a positive biological effect; protection against challenge with live pathogenic bacteria.

Immunizations of white CF1 mice were undertaken as described in Example 4. The mice were challenged on day 40 by intraperitoneal injection with approximately 2,000 microorganisms of N. meningitidis B; serotype 2b, strain 80165. Five hours later, the mice were bled, and the number of live bacteria remaining determined as "colony forming units" (CFU/ml). The N-propionyl and N-butanoyl meningococcal B polysaccharides were prepared by reaction of the de-N-acetylated polysaccharide with the appropriate acid anhydride, as described above. The results are presented in Table 3.

TABLE 3

Active protection of mice with N-propionyl (NPr) and N-butanoyl (NBu) modified meningococcal B polysaccharide-tetanus toxoid (TT) conjugates and octadecyl tyrosyl glycine adjuvant. Adjuvant concentration is 0.75 mg/ml.

| Immunogen | CFU/ml | No. mice bacteremic |
|---|---|---|
| 1) Adjuvant | 3584 | 5/5 |
| 2) NPr polysaccharide | 2664 | 5/5 |
| 3) NPr polysaccharide TT conjugate | 640 | 4/5 |
| 4) NPr polysaccharide TT conjugate + Adjuvant | 0 | 0/5 |
| 5) NBu Polysaccharide TT conjugate + Adjuvant | 296 | 1/5 |

The results in Table 3 show that the adjuvant and polysaccharide conjugate vaccine affords the best protection. The adjuvant is not effective alone.

We claim:

1. A vaccine composition comprising a bacterial polysaccharide protein conjugate and an effective amount of at least one adjuvant of the formula:

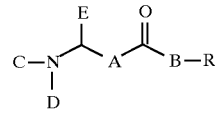

wherein

C is selected from the group consisting of hydrogen, an amino acid residue, and a peptide residue;

D is selected from the group consisting of hydrogen and any other pharmaceutically acceptable acid;

E is selected from the group consisting of 4-hydroxybenzyl, benzyl, 4-hydroxyphenyl, phenyl, 4-aminobutyl, isopropyl, methyl, hydrogen and a residue of a naturally occurring amino acid;

A is $(CH_2)_n$ oxygen or $CH_2O$ and B is $(CH_2)_n$ or oxygen, wherein n is 0 to 4, with the proviso that A and B are not the same for $(CH_2)_n$ and oxygen; and R is alkyl of 12 to 20 carbon atoms.

2. A composition according to claim 1, wherein said adjuvant comprises an amino acid having an L-configuration.

3. A composition according to claim 1, wherein said adjuvant comprises an amino acid having a D-configuration.

4. A composition according to claim 1, wherein said adjuvant comprises an amino acid mixture of D and L-configurations.

5. A composition according to claim 1, wherein E is selected from the group consisting of 4-hydroxybenzyl, benzyl, 4-hydroxyphenyl, phenyl and hydrogen.

6. A composition according to claim 5, wherein E is 4-hydroxybenzyl.

7. A composition according to claim 1, wherein C is selected from the group consisting of hydrogen, an amino acid and a peptide residue including up to ten amino acid residues.

8. A composition according to claim 7, wherein said peptide residue is selected from a dipeptide and a tripeptide.

9. A composition according to claim 1, wherein the pharmaceutically acceptable acid is selected from the group consisting of hydrochloric, hydrobromic, phosphoric, sulfuric, tartaric, lactic and acetic acid.

10. A composition according to claim 1, wherein said adjuvant comprises an α-amino acid.

11. A composition according to claim 1, wherein said bacterial polysaccharide is coupled to a biological carrier wherein said carrier is selected from the group consisting of tetanus toxoid, diphtheria toxoid, acellular pertussis vaccine (LPF), a cross-reacting material (CRM) and a bacterial protein carrier.

12. A composition according to claim 11, wherein said CRM is $CRM_{197}$.

13. A composition according to claim 1, wherein said bacterial polysaccharide is selected from a capsular polysaccharide, a lipopolysaccharide and a subcapsular surface polysaccharide.

14. A composition according to claim 1, wherein said adjuvant is an ester of an alkyl alcohol containing 14 to 20 carbon atoms and an amino acid, dipeptide or tripeptide.

15. A composition according to claim 14, wherein said adjuvant is octadecyl tyrosine.

16. A composition according to claim 14, wherein said adjuvant is octadecyl tyrosyl glycine.

17. A method of eliciting an immune response in a patient, said method comprising the step of administering to said patient a therapeutically effective amount of a vaccine composition of claim 1.

18. A method according to claim 17, wherein said composition is administered intramuscularly, intradermally, subcutaneously, or by way of nasal delivery.

19. A method according to claim 17, wherein administration of said vaccine composition does not substantially raise IgE antibody levels above preimmunization levels and does increase the ratio of IgG2a to IgG1 antibody relative to the IgG2a to IgG1 ratio resulting from the administration of the vaccine composition without adjuvant.

20. A method of forming a vaccine composition, comprising the step of formulating a bacterial polysaccharide protein conjugate and an adjuvant as defined in claim 1 in amounts sufficient to produce an immunologically effective vaccine composition.

21. A composition according to claim 14, wherein said capsular polysaccharide is isolated from a group consisting of *Haemophilus influenzae, Neisseria meningitidis, Streptococcus pneumonia, Streptococcus agalactiae, Salmonella typhi, Escherichia coli,* and *Staphylococcus aureus.*

22. A composition according to claim 14, wherein said lipopolysaccharide is isolated from a group consisting of *Neisseria meningitidis, Escherichia coli, Salmonella typhi,* and *Pseudomonas aeruginosa.*

23. A composition according to claim 1, wherein said subcapsular polysaccharide is selected from the group consisting of the common polysaccharide antigen (c-substance) of Group A, B and C streptococci and the common polysaccharide antigen (c-substance) of *Streptococcus pneumoniae.*

* * * * *